United States Patent [19]

Kägi et al.

[11] 4,222,739
[45] Sep. 16, 1980

[54] CERTAIN BIS(PHENYL)-BENZODIFURANS

[75] Inventors: Bruno Kägi, Therwil; Géza Kormány, Allschwil; Christian Lüthi, Basel, all of Switzerland

[73] Assignee: Ciba-Geigy Corporation, Ardsley, N.Y.

[21] Appl. No.: 941,429

[22] Filed: Sep. 11, 1978

[30] Foreign Application Priority Data

Sep. 16, 1977 [LU] Luxembourg ............................ 78135

[51] Int. Cl.² .................... D06P 1/00; C07D 307/84; C07D 307/80
[52] U.S. Cl. .................................. 8/648; 252/301.32; 427/158; 260/40 R; 260/40 P; 260/42.21; 260/42.43; 260/42.46; 260/346.71; 8/641
[58] Field of Search .................... 260/346.71; 8/1 W; 252/301.32; 427/158

[56] References Cited

U.S. PATENT DOCUMENTS

| | | | |
|---|---|---|---|
| 3,864,333 | 2/1975 | Sahm et al. | 260/346.22 |
| 3,971,731 | 7/1976 | Hartmann et al. | 252/301.32 |
| 3,993,670 | 11/1976 | Hartmann et al. | 260/346.7 |

OTHER PUBLICATIONS

Dischendorfer et al., Chem. Abstracts, vol. 30, (1936), 5953.
Grinev et al., Chem. Abstracts, vol. 51, (1957), 16408g.
Sugiyama, Chem. Abstracts, vol. 41, (1947), 5506h.

Primary Examiner—Henry R. Jiles
Assistant Examiner—Bernard Dentz
Attorney, Agent, or Firm—Prabodh I. Almaula

[57] ABSTRACT

Benzodifuranes of the formula

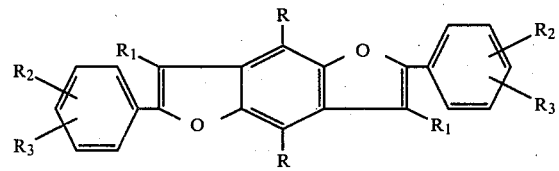

wherein R represents hydrogen, alkyl or halogen, each of $R_1$, $R_2$ and $R_3$ represents hydrogen or different non-chromophoric substituents, with the proviso that at least one of the symbols R, $R_1$, $R_2$ or $R_3$ does not represent hydrogen, processes for their production and the use thereof for whitening organic material of high molecular weight, especially polyester, polyvinyl chloride or polystyrene.

5 Claims, No Drawings

CERTAIN BIS(PHENYL)-BENZODIFURANS

The present invention relates to novel benzodifuranes, processes for their production, and the use thereof for the fluorescent whitening of natural and synthetic organic material.

German Offenlegungsschrift No. 2,306,515 discloses benzodifuranes which are substituted in the 3- and 7-position by a carboxyl group or a modified carboxyl group and which can be used for the fluorescent whitening of organic material.

The present invention provides benzodifuranes of the formula

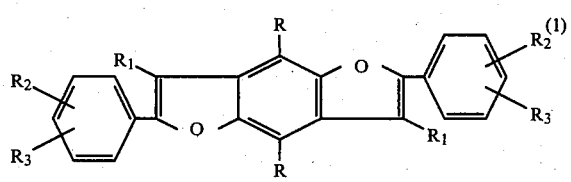

wherein
  R represents hydrogen, alkyl or halogen
  $R_1$ represents hydrogen, alkyl, halogen, cyano, phenyl or, if R is alkyl or halogen, also represents —COOH and the colourless salts thereof, or —COY, wherein Y represents alkoxy, aralkoxy, aryloxy or unsubstituted or mono- or disubstituted amino,
  $R_2$ represents hydrogen, halogen, alkyl, alkoxy, cyano, phenyl, —SO$_3$H and the colourless salts thereof, —SO$_2$X, wherein X represents alkoxy, aralkoxy, aryloxy, unsubstituted or mono- or disubstituted amino, alkyl, phenyl or benzyl, —COOH and the colourless salts thereof, or —COY, wherein Y represents alkoxy, aralkoxy, aryl-oxy or unsubstituted or mono- or disubstituted amino, and
  $R_3$ represents hydrogen, halogen, alkyl or alkoxy, with the proviso that at least one of the symbols R, $R_1$, $R_2$ and $R_3$ must be different from hydrogen.

The term "alkyl" is to be understood as meaning radicals containing 1 to 8, preferably 1 to 4, carbon atoms, and by "halogen" is meant bromine, chlorine, fluorine, preferably chlorine. Possible colourless salts of sulfonic and carboxylic acid are alkaline earth metal, ammonium, amine and alkali metal salts, preferably sodium and potassium salts. Alkoxy radicals contain 1 to 8, preferably 1 to 4, carbon atoms. Aralkoxy radicals contain a total of 7 to 9, preferably 7, carbon atoms. Suitable aryloxy radicals are mononuclear or binuclear radicals, preferably the phenoxy radical. Amino groups can be monosubstituted or disubstituted by alkyl radicals of 1 to 8, preferably 1 to 4, carbon atoms, which in turn can carry hydroxyl and alkoxy groups of 1 to 4 carbon atoms. Two substituents of the nitrogen atom, however, can also together form a 5- to 6-membered saturated ring which can contain a further nitrogen or oxygen atom as ring member. Phenyl and benzyl radicals can be substituted by alkyl of 1 to 4 carbon atoms, alkoxy of 1 to 4 carbon atoms or halogen.

Within the scope of the invention, interesting benzodifuranes are those of the formula

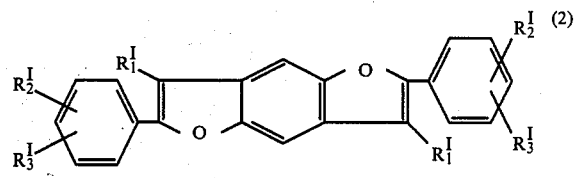

wherein
  $R_1^I$ represents hydrogen, chlorine, lower alkyl or cyano,
  $R_2^I$ represents hydrogen, chlorine, lower alkyl, lower alkoxy, p-phenyl, cyano, —COOH and the colourless salts and lower alkyl esters thereof, or p-SO$_3$H and the colourless salts thereof, and
  $R_3^I$ represents hydrogen or chlorine,
with the proviso that at least one of the symbols $R_1^I$, $R_2^I$ and $R_3^I$ must be different from hydrogen.

Preferred benzodifuranes have the formula

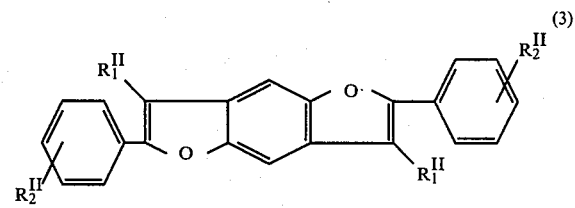

wherein
  $R_1^{II}$ represents hydrogen, chlorine, lower alkyl or cyano, and
  $R_2^{II}$ represents cyano, —COOH and the colourless salts and lower alkyl esters thereof, or p-phenyl.

The most preferred benzodifuranes are those of the formula

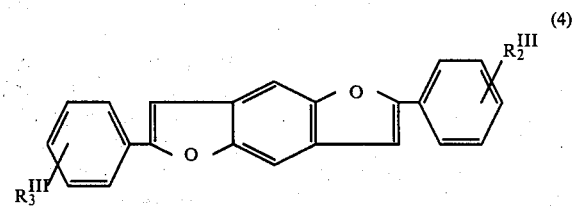

wherein
  $R_2^{III}$ represents ortho- or para-cyano, in particular paracyano.

The compounds of the formulae (1) to (4) can be obtained by methods which are known per se.

Benzodifuranes of the formula

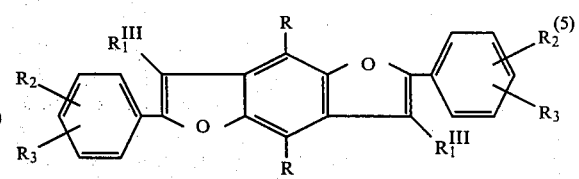

wherein
  R represents hydrogen, alkyl or halogen,
  $R_1^{III}$ represents cyano, phenyl, or if R is alkyl or halogen, also represents —COOH and the colourless salts thereof, or —COY, wherein Y represents alkoxy, aralkoxy, aryloxy or unsubstituted or mono- or disubstituted amino, R$_2$ represents hydrogen, halogen, alkyl, alkoxy, cyano, phenyl, —SO$_3$H and the colourless salts thereof, —SO$_2$X, wherein X represents alkoxy, aralkoxy, aryloxy, unsubstituted or mono- or disubstituted amino, alkyl, phenyl or benzyl, —COOH and the colourless salts thereof, or —COY, wherein Y is as defined above, and R$_3$ represents hydrogen, halogen, alkyl or alkoxy, can be obtained by reacting 2 moles of a compound of the formula

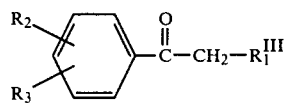 (6)

with one mole of a quinone of the formula

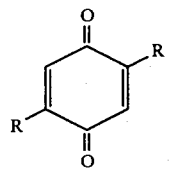 (7)

wherein

R, R$_1^{III}$, R$_2$ and R$_3$ have the above meanings.

Compounds of the formula (6) are known for example from German Offenlegungsschrift No. 2,306,515 or they can be prepared for example by the methods described in Organic Reactions, Vol. 1, 297–302, John Wiley & Sons, Inc., New York, 1947.

The compounds of the formula (5) can be prepared both by means of a single step and a two step process.

In the two step process, the starting material of the formula (6) is first added to the p-benzoquinone in the presence of a base, for example triethylamine, pyridine, piperidine, sodium methylate, a trace of NaOH or KOH, in an inert solvent in the temperature range between 20° and 120° C., preferably between 40° and 80° C. Suitable solvents are alcohols, such as methanol, ethanol, dioxan, or aromatic hydrocarbons, for example benzene, toluene or xylene. The product obtained is subsequently cyclised in the temperature range between 50° and 150° C. in one of the above solvents, preferably an aromatic hydrocarbon which enables the water of reaction to be distilled off as an azeotrope, in the presence of an acid catalyst, such as a mineral acid in the form of H$_2$SO$_4$, H$_3$PO$_4$, polyphosphoric acid or a metal chloride. The preferred catalyst is anhydrous zinc chloride.

In the single step procedure, the starting material of the formula (6) is reacted direct to give the benzodifurane compounds in an organic solvent, such as methanol, ethanol, dioxan, diethyl ether, in the presence of an acid catalyst referred to above, at the boiling temperature of the solvent. The system zinc chloride/alcohol is preferred. The benzodifurane compounds of the formula (1) can be easily isolated by crystallisation from the reaction mixtures on account of their low solubility.

Benzodifuranes of the formula (1) wherein R$_1$ is a hydrogen atom, in particular those of the formula

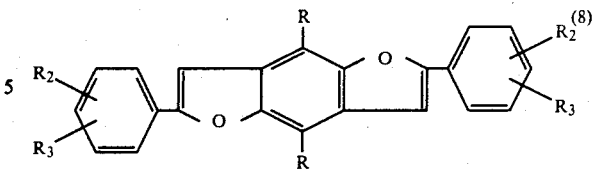 (8)

wherein R, R$_2$ and R$_3$ have the above meanings and at least one of which must be different from hydrogen, can also be obtained by intramolecular condensation of a compound of formula

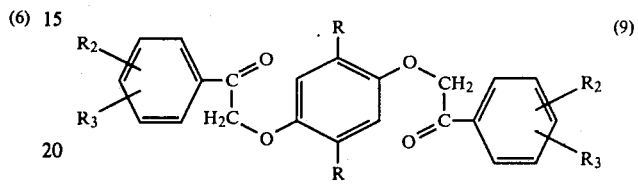 (9)

wherein R, R$_2$ and R$_3$ have the above meanings, in the presence of an acid condensation agent.

A polyphosphoric acid is preferably used as acid condensation agent. Depending on the starting material, the reaction temperature is between 50° and 230° C., preferably between 80° and 180° C.

The reaction products of the above processes can be subjected to yet further known conversation reactions: oxidation, reduction, substitution, for example also sulfonation with sulfonating agents, such as H$_2$SO$_4$, mixtures of H$_2$SO$_4$ and SO$_3$ or chlorosulfonic acid, or those conversion reactions which, starting from molecules which contain sulfo or carboxyl groups, result in compounds containing functionally modified sulfo or carboxyl groups, or the conversion of functionally modified groups of the above kind into other such groups or into the free acids.

The compounds of the formula (9) are obtained in a manner known per se by reaction of the corresponding hydroquinones with β-halogenoacetophenones under conventional etherification conditions.

Benzodifuranes of the formula (1) wherein R$_1$ represents hydrogen, alkyl, chlorine or phenyl, in particular those of the formula

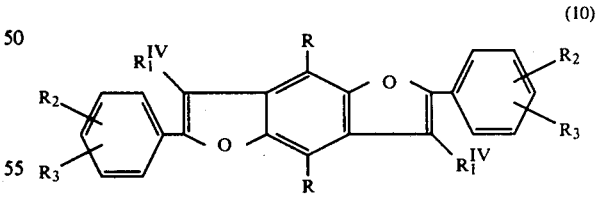 (10)

wherein

R represents hydrogen, alkyl or halogen,

R$_1^{IV}$ represents hydrogen, alkyl, chlorine or phenyl,

R$_2$ represents hydrogen, halogen, alkyl, alkoxy, cyano, phenyl, —SO$_3$H, or —COOH and the colourless salts thereof, or —SO$_3$X or —COY, wherein X represents alkoxy, aralkoxy, aryloxy, unsubstituted or mono- or disubstituted amino, and Y represents alkoxy, aralkoxy, aryloxy or unsubstituted or mono- or disubstituted amino, and R$_3$ represents hydrogen, halogen, alkyl or alkoxy, with the proviso that at least one of the symbols R, $R_1^I$, $R_2$ and $R_3$ must be different from hydrogen, can be obtained by elimination of water from a compound of the formula

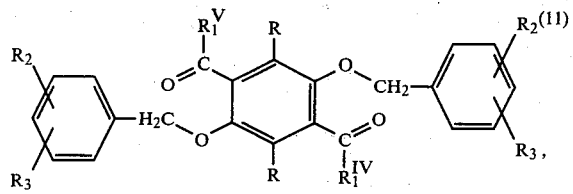

wherein R, $R_2$ and $R_3$ have the above meanings and $R_1^V$ represents hydrogen, alkyl or phenyl, in polar organic solvents, with strongly basic condensation agents, and, if desired, chlorinating a benzodifurane thus obtained, in which $R_1^V$ is hydrogen, to obtain a compound of the formula (10), in which $R_1^I$ is chlorine.

In the compounds of the formula (10), $R_2$ is preferably an electrophilic activating radical, for example cyano, halogen or —COY or —SO$_2$X, wherein X and Y have the above meanings.

Without any restriction being implied, examples of suitable polar solvents are: dimethyl formamide, dimethyl acetamide and hexamethylphosphoric triamide. Mixtures of suitable solvents can also be used.

Suitable strongly basic condensation agents for the cyclisation reaction of the present invention are, inter alia, the alkali metals and alkaline earth metals and their strongly basic compounds as well as the corresponding aluminium compounds, for example the hydroxides, alcoholates, amides or hydrides. Preferably the corresponding sodium or potassium compounds are used, for example potassium hydroxide, potassium tert-butylate or sodium hydroxide. A mixture of different bases can also be used. Normally an equivalent amount of the basic condensation agents is used; however, in some cases they are also used in excess of the stoichiometric proportion, for example in up to 10 times the equivalent amount. The reaction temperature is between 10° and 25° C., preferably between 20° and 160° C. The cyclisation can also be carried out in an alkali melt, for example in a NaOH, KOH or LiOH melt.

The compounds of the formula (11) are obtained in a manner which is known per se by reaction of a compound of the formula (11a)

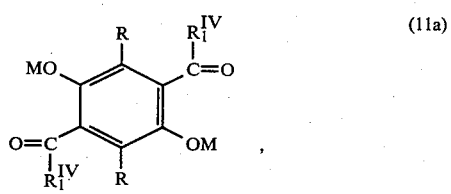

wherein R and $R_1^{IV}$ have the given meanings and M represents an alkali metal cation or alkaline earth metal cation, with a compound of the formula

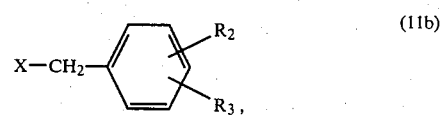

wherein $R_2$ and $R_3$ have the given meanings and X represents the anion of an inorganic acid, preferably of a hydrohalic acid.

Benzodifuranes of the formula (10) can often be obtained in better yield by splitting off an amine ENH$_2$ from a compound of the formula

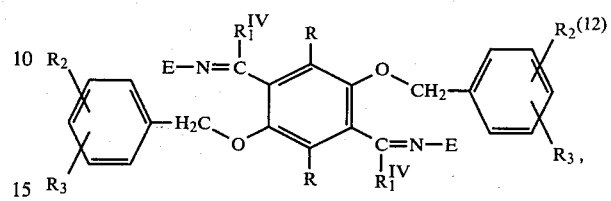

wherein R, $R_1^{IV}$, $R_2$ and $R_3$ have the given meanings and E represents an organic radical which is attached through a tertiary carbon atom to the azomethine nitrogen atom, in the presence of strongly basic condensation agents in polar solvents, accomplished by cyclisation.

Possible organic radicals E are aliphatic, aromatic carbocyclic or heterocyclic radicals, for example the tertbutyl, phenyl or α- and β-naphthyl radical, and also the nuclear substitution products of these aromatic radicals. As these radicals are split off during the reaction as amines, the presence of substituents is in general not advantageous. However, substituents which do not interfere with the reaction, for example chlorine atoms, alkyl groups of 1 to 4 carbon atoms or hydroxyalkyl groups of 2 to 4 carbon atoms, may be present, for example in phenyl radicals. Preferred radicals E are the phenyl radical and a phenyl radical which is substituted by a chlorine atom.

This process is particularly suitable for the production of benzodifuranes of the formula (10), wherein $R_2$ represents a non-activating radical, for example alkyl or alkoxy.

Certain substitutions of compounds falling under formulae (1) to (3) can also be effected by the subsequent introduction of substituents into the cyclised benzodifurane, or by subsequent conversion.

Thus benzodifuranes of the formula (1), wherein $R_1$ represents halogen, are obtained in a manner which is known per se by subsequent halogenation, for example with sulfonyl chloride.

Sulfo groups can also be introduced into the terminal phenyl radicals, for example by subsequent sulfonation of the basic structure, the substitution being preferably in the para-position.

With regard to sulfo groups and carboxylic acid groups and the functional derivatives thereof, it applies generally that they are often usefully obtained only after the cyclisation by modification of suitable groups by methods which are known per se. Thus the carboxylic acid groups for example can be obtained by subsequent saponification of the cyano group in the end product which can in turn be converted, for example via an acid chloride, into esters or amides. The alkylsulfonyl group can also be obtained by oxidation of an alkylmercapto or alkylation of a sulfinic acid group, which can be obtained via a sulfo chloride, at the end structure.

The novel compounds defined above exhibit a more or less pronounced fluorescence in the dissolved or finely divided state. They can be used for whitening a wide variety of synthetic, regenerated man-made or natural organic materials or substances which contain such organic materials.

Without any restriction being implied by the following classification, examples of organic materials which can be treated with fluorescent whitening agents are:

I. Synthetic materials of high molecular weight:
   (a) polymerisation products based on organic compounds containing at least one polymerisable carbon-carbon double bond, that is to say their homopolymers or copolymers as well as their after-treatment products, for example, cross-linking, grafting or degradation products, polymer blends, or products obtained by modification of reactive groups, for example polymers based on α,β-unsaturated carboxylic acids or derivatives of such carboxylic acids, especially on acrylic compounds, for example acrylates, acrylic acid, acrylonitrile, acrylamides and their methacrylic analogues), on olefin hydrocarbons (for example ethylene, propylene, styrenes or dienes and also ABS polymers), and polymers based on vinyl and vinylidene compounds (for example vinyl chloride, vinyl alcohol and vinylidene chloride);
   (b) polymerisation products which can be obtained by ring opening, for example, polyamides of the polycaprolactam type, and also polymers which are obtained both by polyaddition and by polycondensation, for example polyethers or polyacetals;
   (c) polycondensation products or precondensates based on bifunctional or polyfunctional compounds with condensable groups, their homocondensation and co-condensation products, and after-treatment products, for example polyesters, especially saturated polyesters (for example ethylene glycol, terephthalic acid polyester) or unsaturated polyesters (for example maleic acid-dialcohol polycondensates as well as their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and analogues, polycarbonates and silicones;
   (d) polyadducts, such as polyurethanes (crosslinked and uncrosslinked) and epoxide resins.

II. Regenerated manmade organic materials, for example, cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic materials of animal or vegetable origin, for example based on cellulose or proteins, such as cotton, wool, linen silk, natural film-forming resins, starch and casein.

The organic materials to be whitened can be in the most diverse states of processing (raw materials, semi-finished goods or finished goods). On the other hand, they can be in the form of structures of the most diverse shapes, for example predominantly three-dimensional structures such as sheets, profiles, injection mouldings, various machined articles, chips, granules or foams, and also predominantly two-dimensional structures, such as films, sheets, lacquers, coatings and impregnations or predominantly one dimensional bodies, such as filaments, fibres, flocks and wires. The above materials can, on the other hand, also be in an unshaped state, in the most diverse homogeneous or inhomogeneous forms of division, as for example in the form of powders, solutions, emulsions, dispersions, latices, pastes or waxes.

Fibrous materials can be, for example, in the form of endless filaments (stretched or unstretched), staple fibres, flocks, hanks, textile filament yarns, threads, nonwovens, felts waddings, flocked structures or woven textile or bonded textile fabrics, knitted fabrics, and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be whitened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of whitening agent used, it can be advantageous to carry out the treatment in a neutral or alkaline or acid bath. The treatment is usually carried out at temperatures of 20° to 140° C., for example at the boiling point of the bath or near it (about 90° C.).

Solutions or emulsions in organic solvents can also be used for the finishing according to the invention of textile substrates, as is practised in the dyeing industry in so-called solvent dyeing (pad-thermofixation application, or exhaust dyeing methods in dyeing machines).

The fluorescent whitening agents of the present invention can further be added to, or incorporated in, the materials before or during their shaping. Thus they can for example be added to the compression moulding composition or injection moulding composition during the manufacture of films, sheets (for example incorporated in polyvinyl chloride in a roller mill at elevated temperature) or mouldings.

If manmade synthetic or regenerated manmade organic materials are formed by spinning processes or from spinning solutions/melts, the fluorescent whitening agents can be applied by the following processes:

addition to the starting substances (for example monomers) or intermediates (for example precondensates or prepolymers), that is to say before or during the polymerisation, polycondensation or polyaddition, sprinkling in powder form on polymer chips or granules for spinning solutions/melts, bath dyeing of polymer chips or granules for spinning solutions/melts, metered addition to spinning melts or spinning solutions, and application to the spun tow before stretching.

The fluorescent whitening agents of the present invention can, for example, also be employed in the following use forms:
   (a) in mixtures with dyestuffs (shading) or pigments (coloured pigments or especially, for example, white pigments), or as an additive to dyebaths, printing pastes, discharge pastes or reserve pastes, or for the aftertreatment of dyeings, prints or discharge prints;
   (b) in mixtures with carriers, wetting agents, plasicisers, swelling agents, antioxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, expecially synthetic resin finishes (for example creaseproof finishes such as wash-and-wear, permanent-press or non-iron), as well as flameproof finishes, soft handle finishes, antisoiling finishes or antistatic finishes, or antimicrobial finishes;

(d) incorporation of the fluorescent whitening agents in polymeric carriers (polymerisation, polycondensation or polyaddition products, in a dissolved or dispersed form, for use, for example, in coating agents, inpregnating agents or binders (solutions, dispersions and emulsions) for textiles, nonwovens, papers and leather;

(e) as additives to master batches;

(f) as additives to a wide variety of industrial products in order to render these more marketable (for example improving the appearance of soaps, detergents, pigments);

(g) in combination with other substances with fluorescent whitening properties;

(h) in spinning bath preparations, that is to say as additives to spinning baths which are used for improving the slip for the further processing of synthetic fibres, or from a special bath before the stretching of the fibre;

(i) as scintillators for various purposes of a photographic nature, for example for electrophotographic reproduction of supersensitising;

(j) depending on the substitution, as laser dyes.

If the whitening process is combined with textile treatment or finishing methods, the combined treatment can in many cases advantageously be carried out with the aid of appropriate stable preparations which contain the fluorescent whitener compounds in such a concentration that the desired white effect is achieved.

In certain cases, the fluorescent whitening agents are made fully effective by an aftertreatment. This can be, for example, a chemical treatment (for example acid treatment), a thermal treatment or a combined chemical/thermal treatment. Thus, for example, the appropriate procedure to follow in whitening a number of fibre substrates, for example polyester fibres, with the fluorescent whitening agents of the present invention, is to impregnate these fibres with the aqueous dispersions (or optionally also solutions) of the whitening agents at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperature between 120° and 225° C., for example by heating in a drying chamber, by ironing within the specified temperature range or by treatment with dry, superheated steam. The drying and dry heat treatment can also be carried out in immediate succession or be combined in a single process stage.

The amount of fluorescent whitening agent of the present invention to be used, based on the weight of the material to be whitened, can vary within wide limits. A marked and lasting effect can be obtained even with very insignificant amounts, in certain cases 0.0001 percent by weight. But it is also possible to use amounts of up to 0.8 percent by weight and on occasion, up to 2 percent by weight. For most practical purposes, it is preferable to use amounts between 0.005 and 0.5 percent by weight.

For various reasons it is often advantageous not to use the fluorescent whitening agents by themselves, i.e. pure, but in admixture with a wide variety of assistants and extenders, for example anhydrous sodium sulphate, sodium sulphate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The invention is illustrated by the following Examples, in which the parts and percentages are by weight. Unless otherwise indicated, melting and boiling points are uncorrected.

EXAMPLE 1

13.2 g of sodium hydride (55%, in mineral oil) are suspended in 150 ml of dimethyl formamide. A solution of 29.1 g of 2,5-dihydroxyterephthaldialdehyde in 150 ml of dimethyl formamide are added at 20° to 25° C. in the course of 30 minutes and, after stirring for 3 hours, 64.6 g of α-bromo-p-toluonitrile, dissolved in 300 ml of dimethyl formamide, are added to the reaction mixture at 20° to 25° C. in the course of 1 hour. The batch is stirred for 16 hours at 20° to 25° C. and then heated for a further two hours to 65°–70° C. The reaction mixture is cooled and then poured in 1500 ml of ice-water, neutralised with a small amount of glacial acetic acid, and the precipitate is collected by suction and dried. Recrystallisation from dimethyl formamide yields 49.8 g of the product of the formula

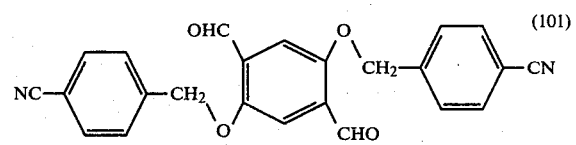

with a melting point of 296°–298° C.

The compounds of the formulae

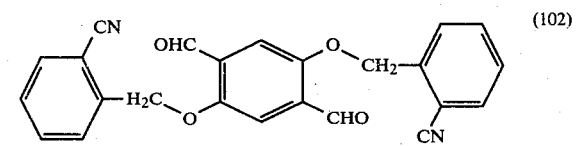

(m.p. 255°–256° C.)

and

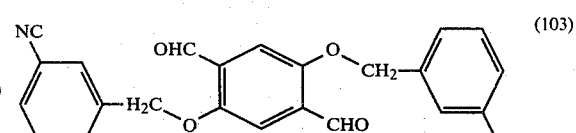

(m.p. 264°–266° C.)

are obtained in similar manner.

13.2 g of compound (101) are suspended in 500 ml of dimethyl formamide and the suspension is heated, under nitrogen, to 125° C. Then 4.2 g of solid potassium hydroxide are added by grams in the course of 15 minutes and the mixture is stirred for a further 15 minutes. The reaction mixture is cooled to 0° C. and the precipitate is collected by suction, washed with a small amount of 2N hydrochloric acid and water and dried.

Recrystallisation from dimethyl formamide affords 6.6 g of intense yellow crystals of the formula NC—⟨⟩—CH=CH—⟨furo-benzo-furo⟩—CH=CH—⟨⟩—CN  (104)

with a melting point of >300° C.
The compound of the formula

HOOC—⟨⟩—CH=CH—⟨furo-benzo-furo⟩—CH=CH—⟨⟩—COOH  (105)

is obtained in a manner which is known per se by saponification of the compound (104).

The compounds of the formulae

⟨⟩(NC)—CH=CH—⟨furo-benzo-furo⟩—CH=CH—⟨⟩(CN)  (106)

(m.p. >300° C.)
and

NC—⟨⟩—CH=CH—⟨furo-benzo-furo⟩—CH=CH—⟨⟩—CN  (107)

(m.p. >300° C.)
are obtained by repeating the above procedure, but using equimolar amounts of the compounds (102) and (103).

EXAMPLE 2

20 g of the compound (104) obtained in Example 1, 30 g of 88% potassium hydroxide and 320 ml of ethanol are reacted for 10 hours at 190° C. in an autoclave. The reaction mixture is cooled and the yellow crystalline precipitate is collected by suction, washed with ethanol and dried, affording 25.1 g of the compound of the formula KOOC—⟨⟩—CH=CH—⟨furo-benzo-furo⟩—CH=CH—⟨⟩—COOK  (201)

with a melting point of >360° C.

EXAMPLE 3

25.1 g of the compound (201) obtained in Example 2 are reacted in chlorobenzene with 22 ml of thionyl chloride in the presence of 0.5 ml of pyridine at 75° C. for 18 hours to give the acid chloride. The reaction mixture is cooled and the precipitate is collected by suction and dried. Recrystallisation from chlorobenzene affords 22 g of the compound of the formula ClOC—⟨⟩—CH=CH—⟨furo-benzo-furo⟩—CH=CH—⟨⟩—COCl  (301)

with a melting point of 339° C. (with decomp.).

EXAMPLE 4

4.35 g of the compound obtained in Example 3 are suspended in 100 ml of dichlorobenzene. To the suspension are added 7.4 g of n-butanol and 4 g of pyridine and the mixture is reacted for 2 hours at 180° C. The reaction mixture is cooled and the precipitate is collected by suction and dried, affording 2.8 g of the compound of the formula $C_4H_9$OOC—⟨⟩—CH=CH—⟨furo-benzo-furo⟩—CH=CH—⟨⟩—COO$C_4H_9$  (401)

One recrystallisation from xylene and decolouration with activated charcoal yields a pale yellowish green product with a melting point of 283°–343° C. (gradual, with decomp.).

The compounds of the formulae $C_2H_5$($CH_3$)CHOOC—⟨⟩—CH=CH—⟨furo-benzo-furo⟩—CH=CH—⟨⟩—COOCH($CH_3$)—$C_2H_5$  (402)

(gradual melting from 224°–274° C., with decomp.) and

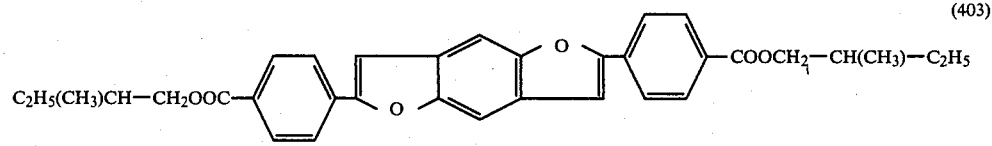

(gradual melting from 264°–332° C., with decomp.) are obtained by repeating the above procedure, but using sec-butanol or 2-methyl-1-butanol instead of n-butanol.

EXAMPLE 5

20 g of polyphosphoric acid (approx. 82% $P_2O_5$) are treated with 5 g of the compound of the formula

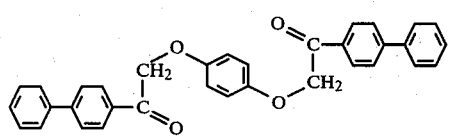

(m.p. 205°–207° C.), and the reaction mixture is subsequently stirred under nitrogen for 4 hours at a bath temperature of 250° to 300° C. The reaction mixture is then cooled and poured onto ice. The precipitate is collected by suction, washed neutral with water, dried and recrystallised from chlorobenzene. Yield: 0.5 g of light yellowish green crystals of the formula

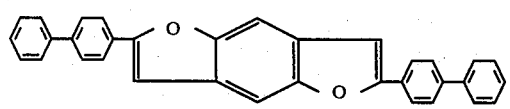

with a melting point of >300° C.

The compounds of the formulae

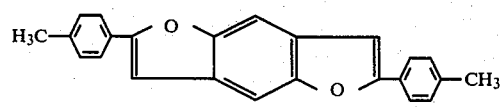

(m.p. 222°–224° C.) and

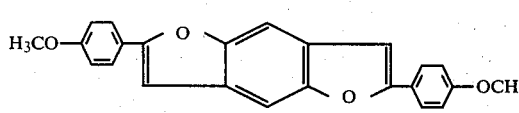

are obtained by using equimolar amounts of the compounds of the formulae

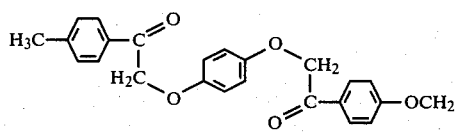

(m.p. 199°–201° C.) and

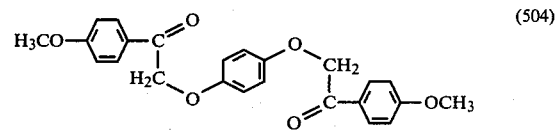

(m.p. 212°–213° C.).

EXAMPLE 6

5.5 g of 1,4-benzoquinone and 15.9 g of ethyl p-chlorobenzoyl acetate are dissolved in 30 ml of acetone. With stirring, 13.6 g of anhydrous $ZnCl_2$, dissolved in 50 ml of acetone, are added dropwise at reflux temperature in the course of 60 minutes. The mixture is stirred at this temperature for 8 hours, then cooled. The precipitate is collected by suction and washed with a small amount of cold acetone, affording 7.8 g of the product of the formula

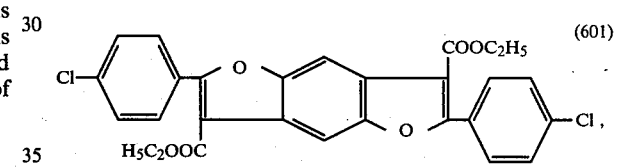

which melts at 294°–296° C. after recrystallisation from chlorobenzene with the aid of fuller's earth.

2.6 g of the compound (601) are saponified in a manner which is known per se. Recrystallisation from dimethyl formamide/alcohol yields 1.8 g of the product of the formula

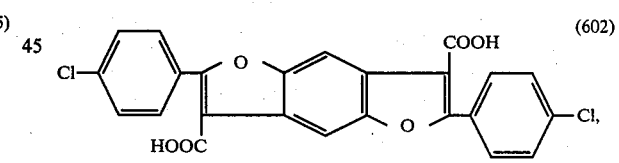

which melts at >360° C.

1.2 g of the compound (602) are heated with 0.2 g of copper powder, under nitrogen and with stirring, to about 300° C., whereupon the product of the formula

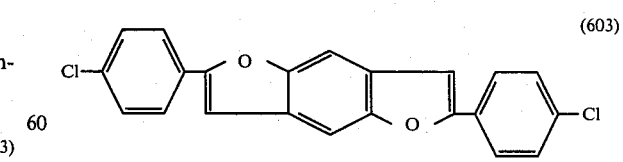

sublimes. Recrystallisation with the aid of fuller's earth yields 0.8 g of light yellowish green, felted needles, which melt at >360° C.

EXAMPLE 7

3.1 g of the compound of the formula

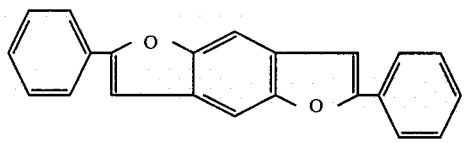
(701)

are stirred in 20 ml of 96% sulfuric acid at 20° C. The sulfonated product is neutralised with aqueous sodium hydroxide and evaporated to dryness, yielding the compound of the formula

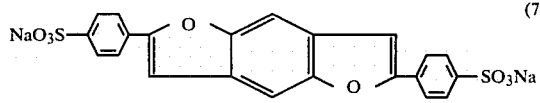
(702)

with a melting point of >360° C.

EXAMPLE 8

3.1 g of the compound of the formula

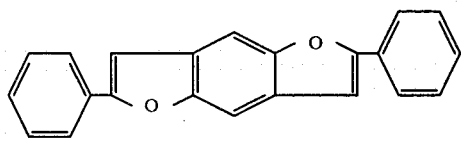
(801)

(m.p. 350°-351° C.)
which is prepared in a manner known per se, are dissolved in 500 ml of carbon tetrachloride. Then 3.2 g of chlorosuccinimide and a catalytic amount of dibenzoyl peroxide are added to the solution. The reaction mixture is irradiated for 8 hours with UV light and refluxed. The yellow suspension is filtered warm, the solution is concentrated, and 100 ml of nonane are added to the residue at 90° C. Recrystallisation yields 1.2 g of the compound of the formula

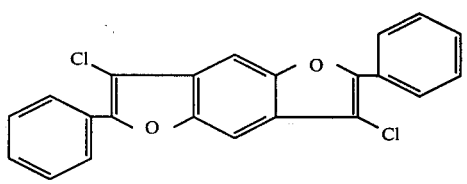
(802)

in the form of light yellow crystals with a melting point of 264°-265° C.

The compound of the formula

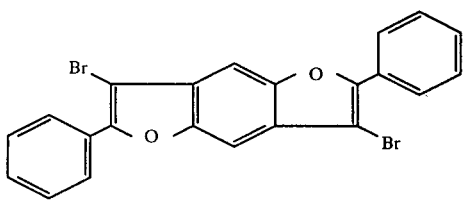
(803)

is obtained by repeating the above procedure, but using an equimolar amount of bromosuccinimide instead of chlorosuccinimide. Melting point: 264°-265° C.

EXAMPLE 9

In a round-bottom flask, equipped with air cooler, 1.6 g of pyridine, 1.4 g of copper (I) cyanide and 2.4 g of diphenyldibromobenzodifurane of the formula (803) are fused at 130° C. and the reaction mixture is heated for 20 hours at 170°-180° C. The cooled, yellowish grey reaction mixture is dissolved in toluene, the solution is filtered and evaporated to dryness and the residue is charged into a chromatography column packed with silica gel. Elution is effected firstly with a solvent mixture of toluene/hexane (1:1), yielding the compound of the formula

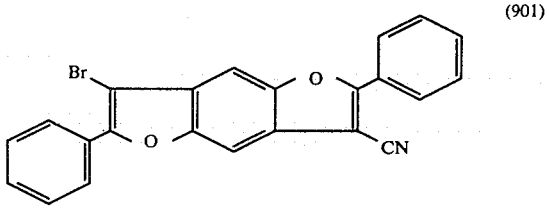
(901)

as a greenish yellow product with a melting point of 266°-268° C. (after recrystallisation from nonane). Further elution is performed with a solvent mixture consisting of toluene/ethyl acetate (7:3), yielding the compound of the formula

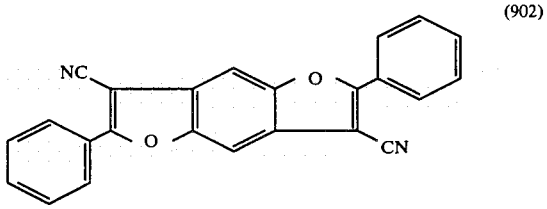
(902)

as a yellow product with a melting point of 312°-315° C. (after recrystallisation from nonane).

EXAMPLE 10

45.8 g of sodium hydride (55%, in mineral oil) are suspended in 600 ml of dimethyl formamide. With cooling, a solution of 97 g of 2,5-diacetylhydroquinone in 500 ml of dimethyl formamide is added to the suspension at 25° C. in the course of 50 minutes and the resulting red suspension is stirred for 3 hours at room temperature. With stirring and cooling, a solution of 215.6 g of p-bromomethylbenzonitrile in 800 ml of dimethyl formamide is then added dropwise at 25° C. in the course of 2 hours to the suspension. The reaction mixture is stirred for 2 hours at room temperature, then reacted for 16 hours at 60° C., and, after cooling, poured into 5 liters of water. The solution is neutralised with acetic acid and the precipitate is collected by suction and dried. Recrystallisation from isopropanol affords 85 g of the light yellow product of the formula

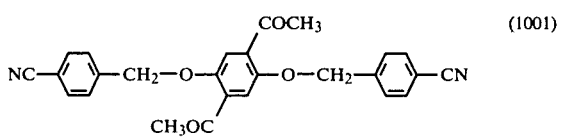
(1001)

with a melting point of 140°-141° C.

12.7 g of the above compound are dissolved in 250 ml of dimethyl formamide. Then 7.4 g of tert-potassium butylate are added in portions at 25° C. with cooling and the brownish violet suspension is stirred for 4 hours at room temperature. The mixture is diluted at room temperature with 750 ml of methanol and the precipitate is collected by filtration and washed thoroughly with methanol. The light yellow product is recrystallised twice from a solvent mixture of dimethyl formamide/ethanol (1:3), affording 9 g of the compound of the formula

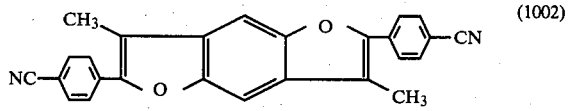

in the form of pale yellow crystals with a melting point of 320°-325° C.

The 2,5-diacetylhydroquinone of the formula

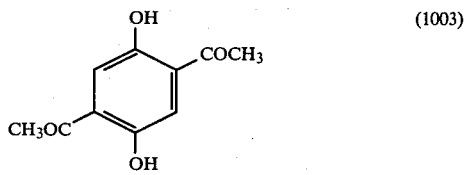

used as starting material for the production of the compound of the formula (1001) can be obtained as follows:

With stirring and cooling, 535 g of aluminium chloride are added at 25° C. to 750 ml of nitrobenzene and 400 g of acetyl chloride, dissolved in 250 ml of nitrobenzene, are introduced into the orange brown suspension in the course of 20 minutes. With further cooling and stirring, 250 g of 1,4-dimethoxybenzene, dissolved in 500 ml of nitrobenzene, are added dropwise to the light brown solution at 20° to 25° C. in the course of 60 minutes and the reaction mixture is stirred for 27 hours at room temperature. Then a further 133 g of aluminium chloride and 200 g of acetyl chloride are dissolved in the reaction fluid and the batch is stirred for 40 hours at room temperature and for a further 48 hours at 95° C. The resulting brown suspension is cooled to room temperature and poured into a mixture of 5000 g of ice and 2000 ml of concentrated hydrochloric acid. The mixture is allowed to stand for 24 hours. The water phase is decanted off and the nitrobenzene phase is filtered. The black residue is thoroughly stirred in 4000 ml of ethyl acetate and the solution is filtered and concentrated in vacuo, yielding an olive green product in addition to a small amount of nitrobenzene. This product is filtered (dry weight 89 g, m.p. 170°-175° C.), and dissolved warm in 200 ml of dioxan and 40 ml of concentrated hydrochloric acid. The dark red solution is stirred for 1 hour under gentle reflux and allowed to cool for 12 hours to room temperature. The reddish violet crystalline powder (dry weight 71 g, m.p. 177°-181° C.) is recrystallised from chlorobenzene and from a solvent mixture of xylene/nonane (1:1) with the aid of fuller's earth, affording 36 g of the compound of the formula (1003) in the form of yellow crystals with a melting point of 192° C.

EXAMPLE 11

100 parts of a polyester granulat of terephthalic acid-/ethylene glycol polyester are homogeneously mixed with 0.05 part of one of the compounds of the formulae (104), (106), (107), (401), (402), (403), (502) or (1002) in a roller vessel. With stirring, the mixture is fused at 285° C. and spun through conventional spinnerets. Strongly whitened polyester fibres are obtained. The above compounds can also be added to the polyester before or during the polycondensation.

EXAMPLE 12

A polyester fabric (Dacron ®) is padded at room temperature with an aqueous dispersion which contains, per liter, 2 g of a fluorescent whitening agent of the formula (106) or (401) and 1 g of an adduct of about 8 moles of ethylene oxide and 1 mole of p-tert-octylphenol. The liquor pick-up is 60 to 70%. The fabric is dried at 100° C. and then heated for 10 seconds to 220° C. The treated fabric has a strong white effect of good lightfastness.

EXAMPLE 13

100 parts of polystyrene and 0.1 part of the compounds of the formulae (105), (107), (401), (402), (403), (502), (506) or (902) are fused, with the exclusion of air, for 20 minutes at 210° C. in a tube measuring 1 cm in diameter. After cooling, a whitened polystyrene composition of good lightfastness is obtained.

EXAMPLE 14

A homogeneous mixture of 100 parts of polyvinyl chloride, 3 parts of a stabiliser (Advastat BD 100 ®: Ba/Cd complex), 2 parts of titanium dioxide, 59 parts of dioctyl phthalate, and 0.01 to 0.2 part of a compound of the formulae (107), (401), (402), (403), (505), (506), (603), (902) or (1022) are rolled out to a sheet on a calendar at 150° C. to 155° C.

The resulting opaque polyvinyl chloride sheet possesses a substantially higher white content than a sheet which does not contain the fluorescent whitening agent.

What is claimed is:

1. A benzodifuran of the formula

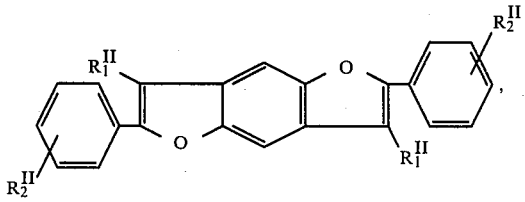

wherein
$R_1^{II}$ represents hydrogen, chlorine, lower alkyl or cyano, and
$R_2^{II}$ represents cyano, —COOH and the colourless salts and lower alkyl esters thereof, or p-phenyl.

2. A benzodifuran according to claim 1 of the formula

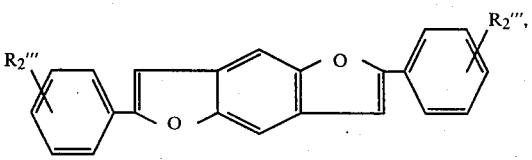

wherein
$R_2^{III}$ represents ortho- or para-cyano.

3. A benzodifuran according to claim 2 of the formula

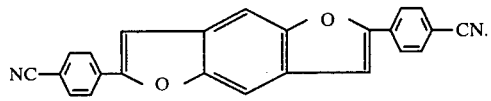

4. A process for the fluorescent whitening of polyester, polyvinyl chloride or polystyrene, which comprises incorporating in said materials or applying to the surface thereof, compounds as defined in claim 1.

5. A process according to claim 4 for the fluorescent whitening of polyester spinning melts and/or solutions.

* * * * *

UNITED STATES PATENT AND TRADEMARK OFFICE
CERTIFICATE OF CORRECTION

PATENT NO. : 4,222,739
DATED : September 16, 1980
INVENTOR(S) : Bruno Kagi, Geza Kormany and Christian Luthi It is certified that error appears in the above-identified patent and that said Letters Patent are hereby corrected as shown below:

In claim 1, column 18, lines 42-50 in the structural formula in both occurrences, " $R_1^{II}$ " should read -- $R_1''$ --; and in both occurrences, " $R_2^{II}$ " should read -- $R_2''$ --; and in line 53, " $R_1^{II}$ " should read -- $R_1''$ --; and in line 55, " $R_2^{II}$ " should read -- $R_2''$ --.

In claim 2, column 18, line 67, " $R_2^{III}$ " should read -- $R_2'''$ --.

Signed and Sealed this

Ninth Day of December 1980

[SEAL]

Attest:

SIDNEY A. DIAMOND

Attesting Officer

Commissioner of Patents and Trademarks